(12) United States Patent
Scorza et al.

(10) Patent No.: US 7,151,203 B2
(45) Date of Patent: *Dec. 19, 2006

(54) **DISEASE RESISTANCE IN *VITIS***

(75) Inventors: Ralph Scorza, Sheperdstown, WV (US); Dennis J. Gray, Howey-in-the-Hills, FL (US)

(73) Assignees: University of Florida Research Foundation, Inc., Gainesville, FL (US); The United States of America as represented by the Secretary of Agriculure, Washington, DC (US)

( * ) Notice: Subject to any disclaimer, the term of this patent is extended or adjusted under 35 U.S.C. 154(b) by 235 days.

This patent is subject to a terminal disclaimer.

(21) Appl. No.: 10/441,669

(22) Filed: May 19, 2003

(65) Prior Publication Data
US 2003/0182686 A1    Sep. 25, 2003

Related U.S. Application Data

(63) Continuation of application No. 09/876,202, filed on Jun. 6, 2001, now abandoned, which is a continuation of application No. 09/511,606, filed on Feb. 23, 2000, now abandoned, which is a continuation of application No. 09/452,577, filed on Dec. 1, 1999, now abandoned, which is a continuation of application No. 08/878,750, filed on Jun. 19, 1997, now Pat. No. 6,232,528.

(60) Provisional application No. 60/020,569, filed on Jun. 26, 1996.

(51) Int. Cl.
*C12N 15/09*  (2006.01)
*C12N 15/82*  (2006.01)
*C12N 15/00*  (2006.01)
*A01H 5/00*   (2006.01)

(52) U.S. Cl. .................. 800/279; 800/278; 800/298; 435/419; 435/460; 435/430.1; 435/431

(58) Field of Classification Search ............... 800/288, 800/279, 298, 278, 295; 435/69.1, 468, 419, 435/430.1, 431
See application file for complete search history.

(56) References Cited

U.S. PATENT DOCUMENTS

| | | | |
|---|---|---|---|
| 5,300,629 A | 4/1994 | Casteels et al. | |
| 5,348,743 A | 9/1994 | Ryals et al. | |
| 5,424,395 A | 6/1995 | Bascomb et al. | |
| 5,548,075 A | 8/1996 | Reed et al. | |
| 5,597,945 A | 1/1997 | Jaynes et al. | |
| 5,597,946 A | 1/1997 | Jaynes et al. | |
| 5,631,007 A | 5/1997 | Ryals et al. | |
| 5,824,861 A | 10/1998 | Aldwinckle et al. | |
| 6,232,528 B1 * | 5/2001 | Scorza et al. | 800/279 |

FOREIGN PATENT DOCUMENTS

WO    WO 94 07356    4/1994

OTHER PUBLICATIONS

GenBank Accession No. D11113.
GenBank Accession No. D11114.
GenBank Accession No. D25320.

(Continued)

*Primary Examiner*—Medina A. Ibrahim
(74) *Attorney, Agent, or Firm*—Saliwanchik, Lloyd & Saliwanchik

(57) ABSTRACT

Disclosed are methods for producing grape plants having resistance to bunch rot disease or *Botrytis* or both. Also disclosed are grape plants having resistance to bunch rot disease or *Botrytis* or both, wherein the plants express a cecropin B peptide Shiva-1.

20 Claims, 4 Drawing Sheets pBPRS1

OTHER PUBLICATIONS

GenBank Accession No. D25321.
GenBank Accession No. M10309.
GenBank Accession No. X16972.
Allefs et al., "*Erwinia* soft rot resistance of potato cultivars transformed with a gene construct coding for antimicrobial peptide cecropin B is not altered," *American Potato Journal*, 72:437-445 (1995).
Arce, P. et al., "Enhanced resistance to bacterial infection by *Erwinia carotovora* subsp. *atroseptica* in transgenic potato plants expressing the attacin or the cecropin SB-37 genes," *Amer J of Potato Res*, 76:169-177 (1999).
Arrowood et al., "In Vitro Activities of Lytic Peptides against the Sporozoites of *Cryptospordium parvum*," *Antimicrobial Agents in Chemotherapy* 35:224-227 (1991).
de Carvalho et al., "Suppression of beta-1,3-glucanase transgene expression in homozygous plants," *The EMBO Journal*, 11:2595-2602 (1992).
Colby et al., "Cellular differences in *agrobacterium* susceptibility and regenerative capacity restrict the development of transgenic grapevines", *J. Amer. Soc. Hort. Sci.*, 116:356-361 (1991).
Finnegan et al., "Transgene inactivation: Plants fight back!," *Bio/Technology*, 12:883-888 (1994).
Florack, D. et al., "Expression of giant silkmoth cecropin B genes in tobacco," *Transgenic Research* 4:132-141 (1995).
Gray et al., "Grape", *Biotechnology of Perennial Fruit Crops*, 9:229-262 (1992).
Gunshefski et al., "In Vitro Antimicrobial Activity of Shiva-11 Against Ocular Pathogens," *Cornea* 13:237-242 (1994).
Hightower et al., "The expression of cecropin peptide in transgenic tobacco does not confer resistance to *pseudomonas syringae* pv *tabaci*," *Plant Cell Reports*, 13:295-299 (1994).
Hill et al., "Multiplication and movement of *Xylella fastidiosa* within grapevine and four other plants," *Phytopathology*, 85:1368-1372 (1995).
Hopkins, "Physiological and pathological characteristics of virulent and avlrulent strains of the bacterium that causes Pierce's Disease of the grapevine," *Phytopathology*, 75:713-717 (1985).
Huang, Y. et al., "Expression of an engineered Cecropin gene cassette in transgenic tobacco plants confers disease resistance to *Pseudomonas syringae* pv. *tabaci*," *Phytopathology*, 87:494-499 (1997).
Jaynes, "Use of genes encoding novel lytic peptides and proteins that enhance microbial disease resistance in plants," *Acta Horticultura*, 336:33-39 (1993).
Jaynes et al., " Expression of a cecropin B lytic peptide analog in transgenic tobacco confers enhanced resistance to bacterial wilt caused by *Pseudomonas solanacearum*," *Plant Science*, 89:43-53 (1993).
Matzke et al., "How and why do plants inactivate homologous (Trans)genes?," *Plant Physiol.*, 107:679-685 (1995).
Mullins et al., "*Agrobacterium*-mediated genetic transformation of grapevines: transgenic plants of *Vitis Rupestris* scheele and buds of *Vitis vinifera* L.," *Bio/Technology*, 8:1041-1045 (1990).
Okamoto, M. et al., "Enhanced expression of an antimicrobial peptide sarcotoxin IA by GUS fusion in transgenic tobacco plants," *Plant Cell Physiol.*, 39:57-63 (1998).
Osusky, M. et al., "Transgenic plants expressing cationic peptide chimeras exhibit broad-spectrum resistance to phytopathogens," *Nature Biotechnology*, 18:1162-1166 (2000).
Perl et al., "Establishment of an *Agrobacterium*-mediated transformation system for grape (*Vitis vinifera* L.): The role of antioxidants during grape-*Agrobacterium* interactions," *Nature Biotechnology*, 14:624-628 (1996).
Rodriguez et al., "Effect of a Cecropin-like Synthetic Peptide (Shiva-3) on the Sporogonic Development of *Plasmodium berghei*," *Experimental Parasitology* 80:596-604 (1995).
Scorza et al., "Transformation of grape (*Vitis vinifera* L.) zygotic-derived somatic embryos and regeneration of transgenic plants," *Plant Cell Reports*, 14:589-592 (1995).
Scorza el al., "Producing transgenic 'thompson seedless' grape (*Vitis vinifera* L.) plants," *J. Amer. Soc. Hort. Sci.*, 121:616-619 (1996).
Sharma, A. et al., "Transgenic expression of cecropin B, an antibacterial peptide from *Bombyx mori*, confers enhanced resistance to bacterial leaf blight in rice," *FEBS Letters*, 484:7-11 (2000).
Walker A., "Grape expectations realized," *Nature Biotechnology* 14:582 (1996).
Williams et al., "Growth of 'thompson seedless' grapevines: II. Nitrogen distribution," *Journal of the American Society of Horticultural Science*, 112:330-333 (1987).

* cited by examiner

TomRSV Shiva kb ──1.7    1.3

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
ggttcagggc gggtcctgga ag                                              22

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
gtaaaagcta attaagaggc cacc                                            24

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
atcaaacagg gtatcctgcg                                                 20

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
ttcccaccaa cgctgatc                                                   18
```

DISEASE RESISTANCE IN *VITIS*

CROSS REFERENCE TO RELATED APPLICATION

This application is a continuation of Ser. No. 09/876,202, filed Jun. 6, 2001, now abandoned; which is a continuation of Ser. No. 09/511, 606, filed Feb. 23, 2000, now abandoned; which is a continuation of Ser. No. 09/452,577, filed Dec. 01, 1999, now abandoned; which is a continuation of Ser. No. 08/878,750, filed Jun. 19, 1997, now U.S. Pat. No. 6,232,528, which claims priority from provisional application 60/020,569, filed Jun. 26, 1996.

BACKGROUND OF THE INVENTION

This application relates to disease resistance in *Vitis*.

Grape (*Vitis* spp.) is a deciduous temperate fruit crop of ancient origin. Grape production ($65 \times 10^6$ metic tons) exceeds that of any other temperate fruit crop and ranks after Citrus and banana among all fruit crops worldwide (FAO Production Yearbook, 1990). Grape surpasses all other fruit crops in value due to its multiple uses for fresh fruit, juice, jelly, raisins, and wine. For example, in the United States, seedless grapes represent about 80% and 98% of the total table and raisin grape production, respectively (In: 1994–95: *The Distribution and Per Capita Consumption of California Table Grapes By Major Varieties in the United States and Canada*, California Table Grape Commission, Fresno, Calif. 1995). Only a few seedless cultivars make up this production, of which 'Thompson Seedless' is the most important. This cultivar accounts for the most production of any single grape variety in the United States. In 1992, 'Thompson Seedless' was grown on 263,621 acres in California (In: *California Grape Acreage*, California Agricultural Statistics Service, Sacramento, Calif., 1993). Thirty-five percent of the table grape production in California in 1994 was 'Thompson Seedless' (23,244,683 boxes, 10 kg/box). In 1993, 97% of the grapes grown for raisin production was 'Thompson Seedless' (In: *Raisin Committee Marketing Policy* 1994–95, Raisin Administrative Committee, Fresno, Calif., 1994).

Although *Vitis* spp. is generally considered to have desirable fruit quality, it is susceptible to many pests and diseases, including anthracnose, black rot, botrytis bunch rot, crown gall, downy mildew, eutypa dieback, various nematodes, phomopsis cane and leaf spot, phylloxera, Pierce's disease, and powdery mildew. Hybridization with resistant species has been the only method available to produce resistant cultivars (Galet and Morton, In: *Compendium of Grape Diseases*, R. C. Pearson and A. C. Goheen, eds., APS Press, St. Paul, 1990, pp. 2–3). While improving grape is possible by conventional breeding, it is difficult and time consuming due to the two- to three-year generation cycle, the long period of time required for reliable progeny testing and selection, and inbreeding depression that prohibits selfing (Gray and Meredith, In: *Biotechnology of Perennial Fruit Crops*, F. A. Hammerschlag and R. E. Litz, eds., C.A.B. Intl., Wallingford, U.K. 1992). These characteristics make introgression of desirable traits into existing grape cultivars difficult if not impossible to achieve in an individual breeder's lifetime. Thus, the alternative, and potentially less time-consuming, approach of using gene transfer to insert desirable genes is one approach for improving grapevine cultivars, even considering the time necessary for field testing transgenic lines. The ability to improve the disease or pest resistance or both of a major grape cultivar (e.g., 'Thompson Seedless') offers the possibility of improving a large portion of the grape production in a relatively short time, assuming that cultivar integrity would not be compromised by the transgene or the insertion event. Such a change could also reduce pesticide use for a significant portion of grape production.

SUMMARY OF THE INVENTION

In one aspect, the invention features a method for producing a transgenic plant of the genus *Vitis* having resistance to a plant pathogen. The method, in general, includes the step of transforming a plant cell with a nucleic acid which expresses a lytic peptide, where the expression of such a lytic peptide provides resistance to a plant pathogen. In preferred embodiments, the method further includes propagating a grape plant from the transformed plant cell. In other preferred embodiments, the method involves transforming a plant cell that is a part of a somatic embryo and propagating or regenerating a transgenic grape plant from the transformed somatic embryo. Expression of the lytic peptide confers disease resistance or tolerance or both to grapevine pathogens and pests including, without limitation, bacterial, fungal, and viral pathogens.

In general, *Vitis* is transformed by introducing into a plant cell or somatic or zygotic embryos a nucleic acid that includes a lytic peptide by using *A. tumefaciens*, microprojectile bombardment, or any combination of these methods (for example, by bombarding the plant cell with microprojectiles, followed by infecting the bombarded cells with *Agrobacterium tumefaciens* including a nucleic acid which expresses the lytic peptide).

In preferred embodiments, the method of the invention involves the use of the lytic peptides Shiva-1 or cecropin B or both.

The methods of the invention are useful for providing disease resistance or tolerance or both to a variety of grape plants (for example, *Vitis* spp., *Vitis* spp. hybrids, and all members of the subgenera *Euvitis* and *Muscadinia*), including scion or rootstock cultivars. Exemplary scion cultivars include, without limitation, those which are referred to as table or raisin grapes and those used in wine production such as Cabernet Franc, Cabernet Sauvignon, Chardonnay (e.g., CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Rootstock cultivars that are useful in the invention include, without limitation, *Vitis rupestris* Constantia, *Vitis rupestris* St. George, *Vitis california*, *Vitis girdiana*, *Vitis rotundifolia*, *Vitis rotundifolia* Carlos, Richter 110 (*Vitis berlandieri×rupestris*), 101–14 Millarder et de Grasset (*Vitis riparia×rupestris*), Teleki 5C (*Vitis berlandieri×riparia*), 3309 Courderc (*Vitis riparia×rupestris*), Riparia Gloire de Montpellier (*Vitis riparia*), 5BB Teleki (selection Kober, *Vitis berlandieri×riparia*), SO$_4$ (*Vitis berlandieri×rupestris*), 41B Millardet (*Vitis vinifera×berlandieri*), and 039-16 (*Vitis vinifera×Muscadinia*).

In another aspect, the invention features a transgenic plant or plant cell of the genus *Vitis* transformed with a nucleic acid which expresses a lytic peptide, wherein expression of the lytic peptide provides resistance to a plant pathogen. In preferred embodiments, the transgenic grapevine or cell with the nucleic acid includes an expression vector. Preferably, the transgenic grapevine or cell is *Vitis vinifera* 'Thompson Seedless' and the expression of the lytic peptide provides resistance to the bacterium *Xylella fastidiosa*, the causative agent of Pierce's Disease. In other preferred embodiments, the transgenic grapevine is a somatic embryo, a scion, or a rootstock.

In still another aspect, the invention features a method of transforming *Vitis* with a nucleic acid which expresses a tomato ringspot virus coat protein (TomRSV-CP) gene, where the expression of such a coat protein gene provides resistance to a plant pathogen.

In still another aspect, the invention features a method of transforming *Vitis* with a nucleic acid which expresses a TomRSV-CP gene and a lytic peptide gene, where the expression of such genes in a grapevine provides resistance to a plant pathogen.

The invention also features scions, rootstocks, somatic or zygotic embryos, cells, or seeds that are produced from any of the transgenic grape plants described herein.

By "lytic peptide" is meant a gene encoding a polypeptide capable of lysing a cell. Exemplary lytic peptides include, without limitation, apidaceins, attacins, cercropins (e.g., cercropin B), caerulins, bombinins, lysozyme, magainins, melittins, sapecin, sarcotoxins, and xenopsins.

By "peptide" is meant any chain of amino acids, regardless of length or post-translational modification (for example, glycosylation or phosphorylation).

By "positioned for expression" is meant that the DNA molecule is positioned adjacent to a DNA sequence which directs transcription and translation of the sequence (i.e., facilitates the production of, for example, a lytic peptide).

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. A plant cell, as used herein, is obtained from, without limitation, seeds, suspension cultures, embryos, meristematic regions, callus tissue, leaves, roots, shoots, somatic and zygotic embryos, as well as any part of a reproductive or vegetative tissue or organ.

By "transgenic" is meant any cell which includes a DNA sequence which is inserted by artifice into a cell and becomes part of the genome of the organism which develops from that cell. As used herein, the transgenic organisms are generally transgenic grapevines and the DNA (transgene) is inserted by artifice into the nuclear or plastidic genome. A transgenic grapevine according to the invention contains at least one lytic peptide or TomRSV-CP or both.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

As discussed above, we have discovered that the expression of a lytic peptide provides grapevines with resistance against disease caused by plant pathogens and pests. Accordingly, the invention provides a number of important advances and advantages for viticulturists. For example, by demonstrating that the lytic peptide Shiva-1 is effective against *Xyellela fastidiosa*, the invention facilitates an effective and economical means for protection against Pierce's Disease. Such protection reduces or minimizes the need for traditional chemical practices that are typically used by viticulturists for controlling the spread of plant pathogens and providing protection against disease-causing pathogens in vineyards. In addition, because grape plants expressing one or more lytic peptide gene(s) described herein are less vulnerable to pathogens and their diseases, the invention further provides for increased production efficiency, as well as for improvements in quality, color, flavor, and yield of grapes. Furthermore, because the invention reduces the necessity for chemical protection against plant pathogens, the invention benefits the environment where the crops are grown. In addition, the expression of a lytic peptide gene or TomRSV-CP or both in a grapevine provides resistance to plant pathogens and can be used to protect grapevines from pathogen infestation that reduces productivity and viability. The methods of the invention are useful for producing grapevines having resistance to diseases including, without limitation, Pierce's disease, crown gall, bunch rot, downy and powdery mildews, and viral diseases caused by arabis mosaic virus, grapevine fanleaf virus, tomato ringspot virus, grapevine leafroll associated virus.

Other features and advantages of the invention will be apparent from the following description of the preferred embodiments thereof, and from the claims.

DETAILED DESCRIPTION

The drawings will first be described.

DRAWINGS

Figure 2:
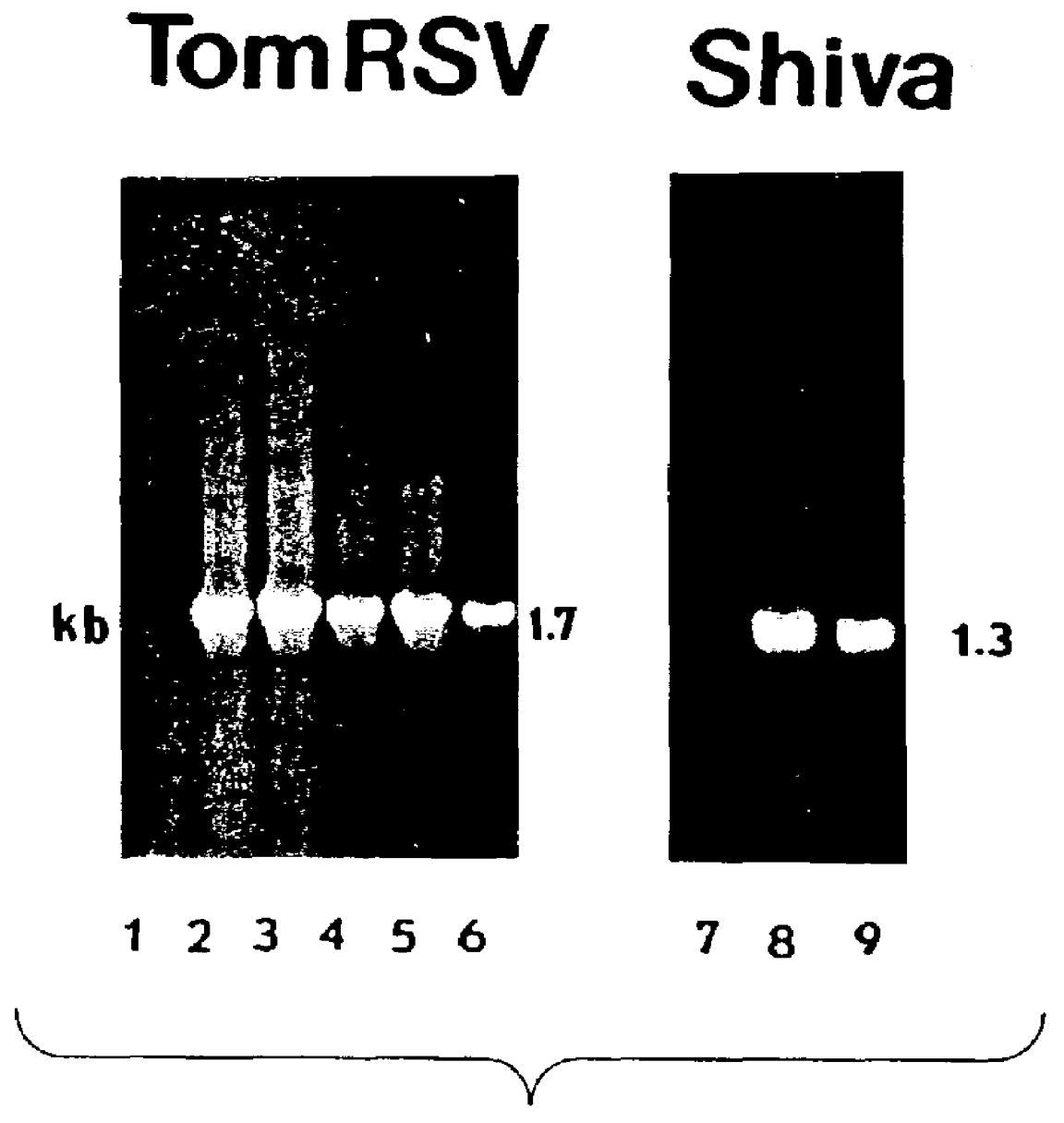
Figure 1A:
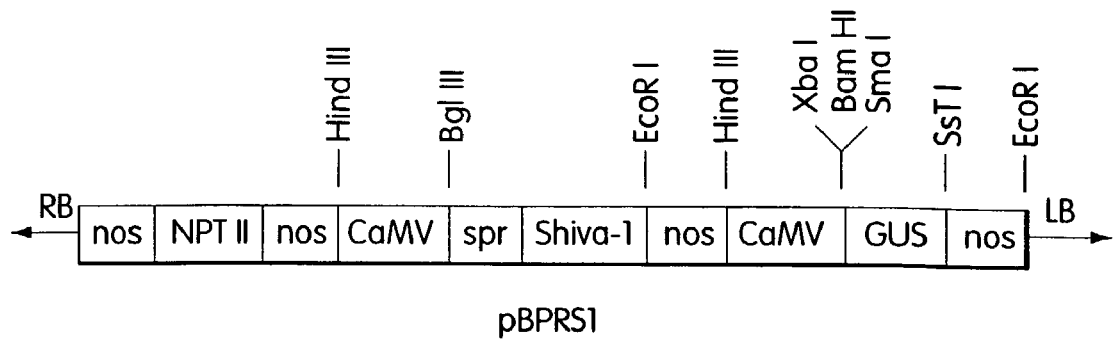
FIG. 1A shows the partial map of the T-DNA region of pBRS1.

FIG. 2 is a photograph showing the results of PCR amplified TomRSV-CP and Shiva-1 fragments from transgenic 'Thompson Seedless' grape plants. PCR analysis using TomRSV-CP primers are as follows: pGA482GG transformant (without the TomRSV-CP gene); lane 2, transformant 3-2; lane 3, transformant 3-3; lane 4, transformant 3S-2; lane 5, transformant 3S-6; lane 6, transformant 3SB-X. PCR analysis using Shiva-1 primers are as follows: lane 7, untransformed 'Thompson Seedless' plant; lane 8, transformant 4-3; lane 9, transformant 4S-2. Transgenic plants 3-2, 3-3, and 4-3, were obtained from *A. tumefaciens* infection alone. Plants 3S-2, 3S-3, 3SB-X, and 4S-2 were obtained from *A. tumefaciens* infection after microprojectile bombardment.

Figure 3:
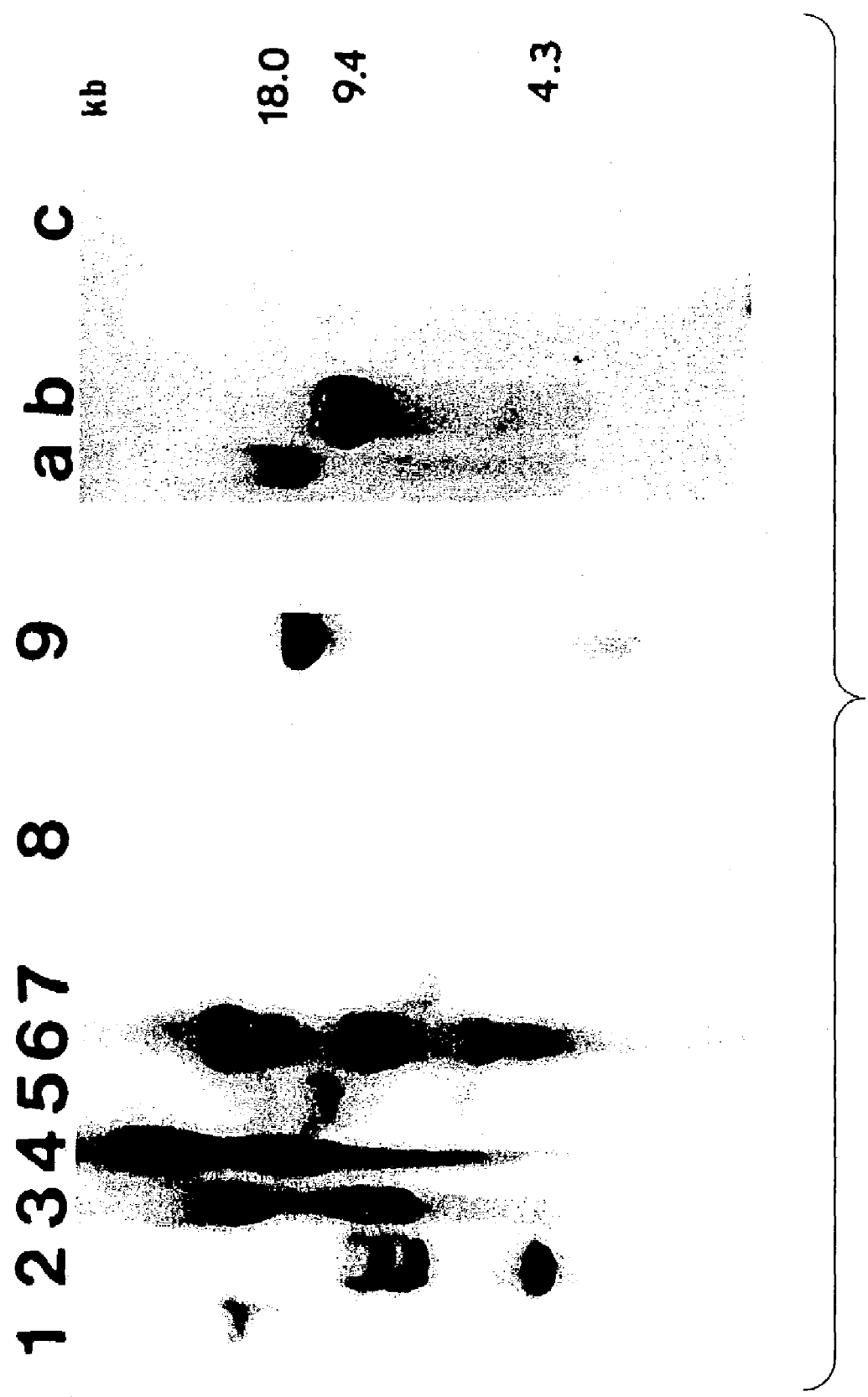

FIG. 3 is a photograph showing the results of a Southern analysis of transgenic 'Thompson Seedless' grape plants. DNA extracted from TomRSV-CP transformants that was digested with EcoRI and probed with a NOS/NPTII fragment is shown in lanes 1 through 9. Lane 1, pGA482GG transformant (control without the TomRSV-CP gene); lane 2, transformant 3-2; lane 3, transformant 3-3 from tissue culture; lane 4, transformant 3-3 from greenhouse leaves (DNA runs slower on gel); lane 5, transformant 3S-2; lane 6, transformant 3S-3; lane 7, transformant 3SB-X; lane 8, untransformed control 'Thompson Seedless'; lane 9, pGA482GG/cpTomRSV plasmid. Shiva-1 transformants digested with BamHI and probed with a NOS/NPTII fragment are shown in lanes a–c. Lane a, transformant 4-3; lane b, transformant 4S-2; lane c, untransformed control 'Thompson Seedless'. Transgenic plants 3-2, 3-3, and 4-3 were obtained from *A. tumefaciens* infection alone. Plants 3S-2, 3S-3, 3SB-X, and 4S-2 were obtained from *A. tumefaciens* infection after microprojectile bombardment.

Figure 4:
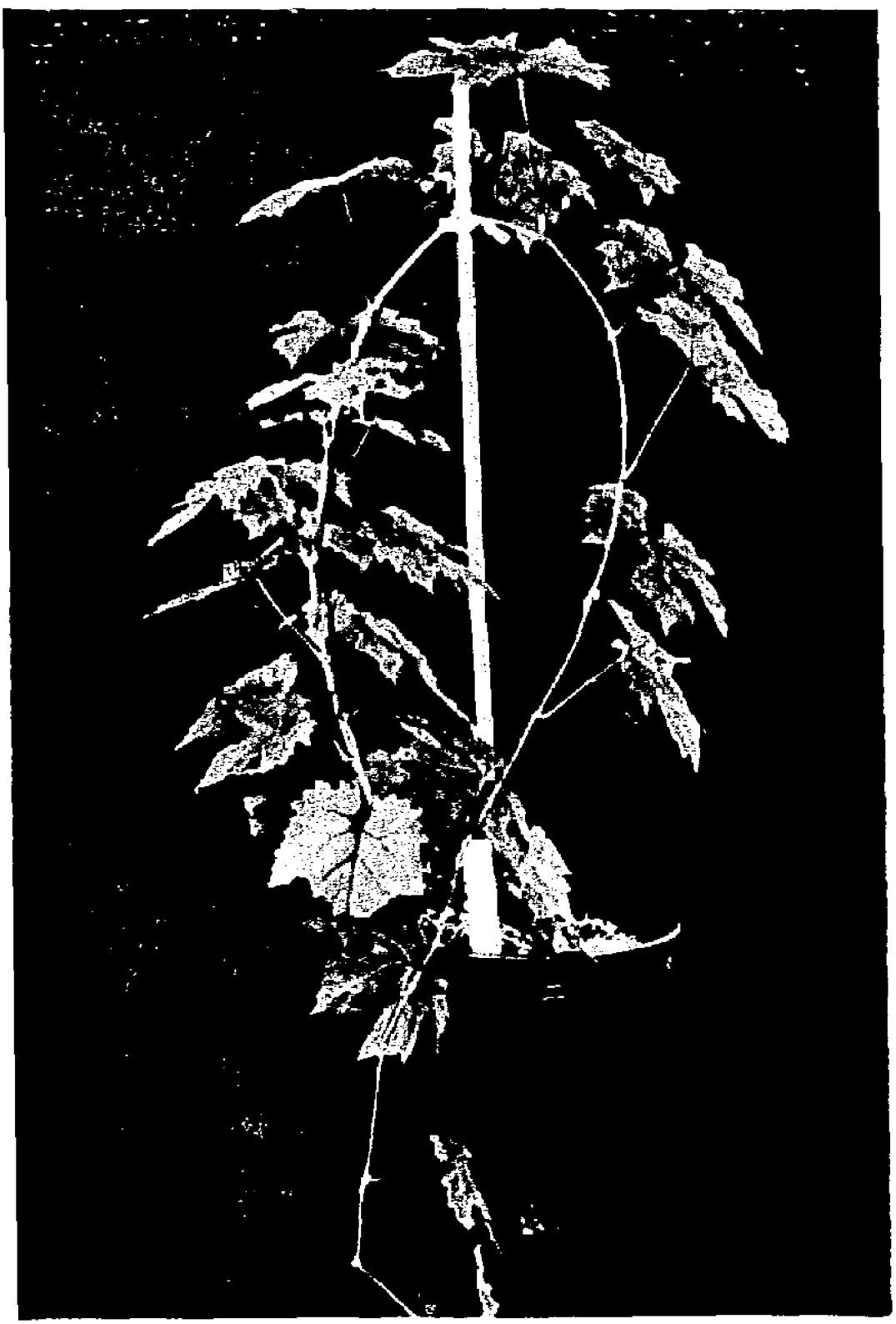

FIG. 4 is a photograph showing a transgenic 'Thompson Seedless' grape plant four months after transfer to the greenhouse.

A description for the production of disease resistant transgenic *Vitis* now follows. Transgenic grape plants expressing either lytic peptide or TomRSV coat protein genes were regenerated from somatic embryos derived from leaves of in vitro-grown plants of 'Thompson Seedless' grape (*Vitis vinifera* L.) plants. Somatic embryos were either exposed directly to engineered *A. tumefaciens* or they were bombarded twice with 1-µm gold particles and then exposed to *A. tumefaciens*. Somatic embryos were transformed with either the lytic peptide Shiva-1 gene or the tomato ringspot virus coat protein (TomRSV-CP) gene. Integration of the foreign genes into these grapevines was verified by growth in the presence of kanamycin (kan), positive β-glucuronidase (GUS) and polymerase chain-reaction (PCR) assays, and Southern analysis. Resistance to Pierce's disease in transgenic plants expressing a lytic peptide was also examined. These examples are provided for the purpose of illustrating the invention, and should not be construed as limiting.

Plant Materials and Culture

Leaves from 'Thompson Seedless' in vitro cultures were used to produce somatic embryos following the method of Stamp et al. (*J. Amer. Hort. Sci.* 115:1038–1042, 1990). Expanding leaves (approximately 0.5 cm long) excised from in vitro-grown shoots were cultured on a modified Nitsch and Nitsch (*Science* 163:85–87, 1969) (NN) medium containing 5 µM of 2,4-D, 1 µM of BA, 60 grams/liter of sucrose, 2 grams/liter of activated charcoal, and 7 grams/liter of agar, pH 5.7. After a three- to twelve-week culture period, somatic embryos formed. These were transferred to a modified Murashige and Skoog (*Plant Physiol.* 15:473–497, 1962) (MS) medium containing 120 grams/liter of sucrose, 2 grams/liter of activated charcoal, and 7 grams/liter of agar, pH 5.7. After three years of continual culture on the modified MS medium with transfers each four to six weeks, somatic embryos were transferred to Emershad and Ramming proliferation (ERP) medium (Emershad and Ramming, *Plant Cell Rpt.* 14:6–12, 1994) for several transfers and then exposed to transformation treatments.

Agrobacterium Strain and Plasmid Descriptions

Figure 1B:
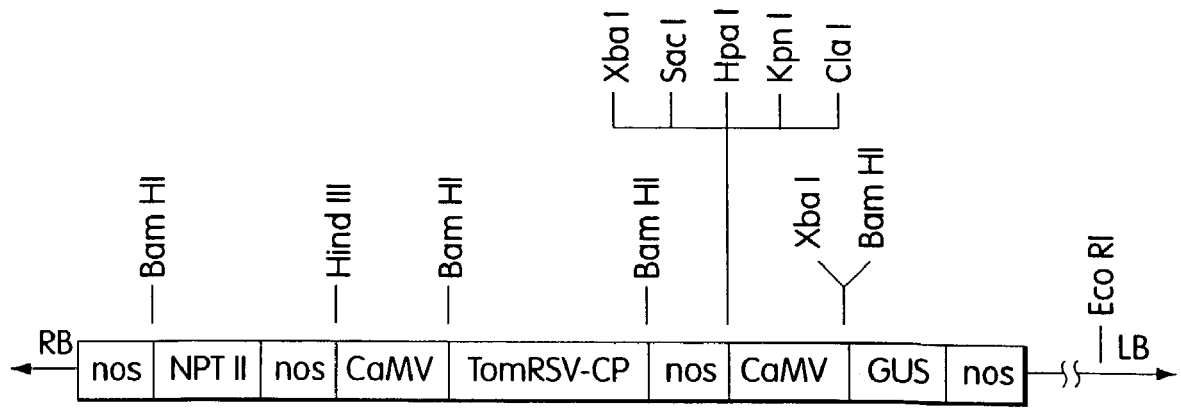
FIG. 1B shows the partial map of the T-DNA region of pGA482GG/cpTomRSV.

For the transformation treatments described below, *A. tumefaciens* strains were EHA101 and EHA105 (Hood et al., *J. Bacterial.* 168:1283–1290, 1986) containing plasmid pGA482GG/cpTomRSV (Slightom, *Gene* 100:252–255, 1991; Slightom et al., *In: Plant Mol. Biol. Man.*, S. B. Gelivn, R. A. Schilperoot, and D. P. S. Verma, eds., Kluwer, Dordrecht, The Netherlands) or pBPRS1, respectively, were used (FIGS. 1A–1B). Both plasmids contained chimeric gusA (β-glucuronidase (GUS)) and kanamycin (Kan) (neomycin phosphotransferase II (NPT II)) genes. Plasmid pGA482GG/cpTomRSV contained the tomato ringsport virus coat protein (TomRSV-CP) gene and pBRPS contained the Shiva-1 lytic peptide gene (Destefano-Beltran et al., *In: The Molecular and Cellular Biology of the Potato*, M. Vayada and W. Parks, eds., C.A.B. Int'l Wallingford, U.K.; Jaynes et al., *Acta Hort.* 336:33–39, 1993).

Cocultivation and Selection

Putative *A. tumefaciens* transformants were cocultivated and selected as described by Scorza et al. (*Plant Cell Rpt.* 14:589–592, 1995). Briefly, *A. tumefaciens* cultures were grown overnight at 28° C. in LB medium containing selective antibiotics for each plasmid. These cultures were centrifuged (5,000 ×g, 10 minutes) and resuspended in a medium consisting of MS salts containing 20 grams/liter of sucrose, 100 µM of acetosyringone, and 1.0 µM of betaine phosphate. The cultures were then shaken for about six hours at 20° C. before use in the transformation treatments that are described below.

Transformation

Somatic embryos were either bombarded with gold microprojectiles and then exposed to *A. tumefaciens* as described by Scorza et al. (*J. Amer. Soc. Hort. Sci.* 119: 1091–1098, 1994) or they were exposed to *A. tumefaciens* without prior bombardment as follows. Microprojectile bombardment was accomplished using the Biolistic PDS-1000/He device (Bio-Rad Laboratories). A total of 700 somatic embryos were separated into groups of 100. Each group was placed onto a 25-mm polycarbonate membrane in the center of a 100-mm petri plate containing ERP medium twenty-four hours before bombardment. Somatic embryos were shot with 1.0-µm diameter gold particles following the general procedures of Sanford et al. (*Meth. Enzmol.* 217: 483–509, 1991) using the parameters described by Scorza et al. (*Plant Cell Rpt.* 14:589–592, 1995). All plates were bombarded twice. Within two hours of bombardment, embryos were cocultivated with *A. tumefaciens*. After bombardment, somatic embryos were immersed in the resuspended *A. tumefaciens* culture that was prepared as described above. After fifteen to twenty minutes, the *A. tumefaciens* culture medium was removed and somatic embryos were placed onto cocultivation medium (ERP medium containing 100 µm acetosyringone). Somatic embryos were cocultivated for two days and then washed with liquid ERP medium (without charcoal) containing 300 µg/ml of cefotaxime and 200 µg/ml of carbenicillin. Somatic embryos were then plated on agar-solidified ERP medium (0.75% agar) with the above-mentioned selective antibiotics. All somatic embryo cultures were allowed to proliferate for two passages (3 weeks each) before being placed onto selection medium. Selection was carried out on ERP medium containing the above specified amounts of cefotaxime and carbenicillin, and 40 µg/ml of kanamycin.

In a second series of transformation experiments, an additional 700 somatic embryos were exposed to *A. tumefaciens* without prior bombardment according to the methods described above.

After cocultivation and selection on ERP medium, putatively transformed embryos were induced to germinate and root on woody plant medium (Lloyd and McCown, *Proc. Intl. Plant Prop. Soc.* 30:421–427, 1981) containing 15 grams/liter of sucrose, 1 µM of BA, 3 grams/liter of agar, pH 6.0 following the protocol of Emershad and Ramming (*Plant Cell Rpt.* 14:6–12, 1994).

Transformation Confirmation

Transformed somatic embryos and shoots produced after somatic embryo germination were assayed by growth on kanamycin-containing medium and through a histological GUS assay (Jefferson, *Plant Mol. Biol. Rpt.* 5:387–405, 1987). Leaf samples of the plants surviving kanamycin selection were observed to produce the characteristic blue GUS positive reaction, indicating the presence and activity of the GUS gene in these plants. Leaves from untransformed control plants showed no blue staining.

Leaves sampled from plants growing in vitro were also cultured for one week in liquid LB medium to assay for the presence of contaminating *A. tumefaciens*. Excised leaves from putative transformants cultured in liquid LB medium were negative for the presence of contaminating *A. tumefaciens*.

After rooting and transfer to the greenhouse, transformed plants were subjected to PCR and Southern analysis. PCR amplification was conducted on DNA isolated from leaves of putatively transformed grape plants. Specific oligonucleotide primers from TomRSV-CP and Shiva-1 gene sequences were used to identify the presence of these genes in DNA from the different clones. For the TomRSV-CP gene, these sequences were the 5' primer 5'-GGTTCAGGGCGGGTCCTGGAAG-3' (SEQ ID NO:1) and 3' primer 5'-GTAAAAGCTAATTAAGAGGCCACC-3' (SEQ ID NO:2); for Shiva-1 gene, the sequences were the 5' primer 5'-ATCAAACAGGGTATCCTGCG-3' (SEQ ID NO:3) and 3' primer 5'-TTCCCACCAACGCTGATC-3' (SEQ ID NO:4). PCR reactions were run using the GeneAmp kit components (Perkin Elmer, Norwalk, Conn.) using the following parameters: 1 minute at 94° C., 1.5 minutes at 65° C., and 2 minutes at 72° C. The first cycle used an additional 3 minutes melt at 95° C. and the last five cycles had a 4 minute extension time period at 72° C. After thirty-five amplification cycles, the PCR products were analyzed by agarose gel electrophoresis and stained with ethidium bromide. PCR analysis using TomRSV-CP and Shiva-1 primers indicated that the thirteen plants that survived kanamycin selection after being exposed to TomRSV-CP or Shiva-1 transformation treatments contained the predicted gene sequences (FIG. 2).

In addition, Southern analysis was used to demonstrate the incorporation of the foreign genes into the grape genome. Southern analysis was carried out using a PCR-generated 1.1-kb NOS/NPTII probe. Digestion with EcoRI was then used to test for unique insertion events that would include segments of grape DNA in pGA482GG/cpTomRSV transformants. BamHI restriction digestion was used for the pBPRS1 (Shiva-1) transformants. Extraction of DNA from transformants followed the procedures of Callahan et al. (*Plant Physiol.* 100:482–488, 1992). Conditions for Southern analysis were described by Scorza et al. (*In Vitro Cell Dev. Biol.* 26:829–834, 1990). The NOS/NPTII probe was radioactively labeled according to standard methods using random primers according to the instructions with the Bio-Rad Random Primer DNA Labeling Kit (BioRad, Hercules, Calif.).

While Southern analysis directly showed only the incorporation of the NPTII gene into the genomes of the assayed grape plants, the close linkage of the TomRSV-CP or the Shiva-1 genes to the NPTII gene coupled with the positive PCR assays for the presence of these genes leads to the conclusion that these plants also contained the TomRSV or Shiva-1 genes. This analysis also indicated that most TomRSV-CP transformants contained multiple copies of the gene insert. Shiva-1 transformants, however, appeared to contain a single insert. Plasmid pGA482GG was used for transferring the TomRSV-CP gene. Previous work using plasmid pGA482GG for transforming grape and other species suggested that multiple copy transformants are common (Scorza et al., *J. Amer. Soc. Hort. Sci.* 119:1091–1098, 1994; Scorza et al., *Plant Cell Rpt.* 14:589–592, 1995).

Previous work examined the use of microprojectile bombardment with *A. tumefaciens* to produce transgenic grape plants. Here we used both microprojectile bombardment and *A. tumefaciens* infection. Although microprojectile bombardment before *A. tumefaciens* infection improved the yield of transformants, the numbers of transformants obtained in this study were too low to be compared with infection with *A. tumefaciens* infection alone. It is apparent, however, that both microprojectile bombardment followed by exposure to *A. tumefaciens* and *A. tumefaciens* infection alone are effective for transforming grape somatic embryos. The overall transformation rate in terms of transgenic plants produced per somatic embryo treated was about 1% (Table 1).

TABLE 1

| Treatment | Somatic Embryos | Putative Transformants | Transformation |
|---|---|---|---|
| *Agrobacterium tumefaciens* alone | | | |
| Control plasmid | 100 | 1 | 1.00 |
| TomRSV-CP | 300 | 2 | 0.67 |
| Shiva-1 | 300 | 2 | 0.67 |
| Particle bombardment plus *A. tumefaciens* | | | |
| Control plasmid | 100 | 1 | 1.00 |
| TomRSV-CP | 300 | 7 | 2.30 |
| Shiva-1 | 300 | 2 | 0.67 |

The results described here differ from our previous report in that we now report transforming grape from somatic embryos derived from leaves, while previously we reported producing transgenic plants from somatic embryos derived from zygotic embryos. The genes transferred include a viral coat protein gene and a lytic peptide gene. To date there have been few reports of transgenic grapevine production, and our results document the successful transformation of a major *Vitis vinifera* scion cultivar.

Disease Resistance

Resistance to Pierce's Disease (PD) has been evaluated in transgenic 'Thompson Seedless' grapevines expressing the lytic peptide Shiva-1. PD is a fatal disease of grapevine known throughout the world. PD kills grapevines by blocking the plant's water-transporting tissue, the xylem. The disease is caused by the bacterium, *Xyllella fastidiosa*, and is spread by a leafhopper, the blue-green sharpshooter that feeds on the xylem fluid of grape. The sharpshooter transmits the bacteria from vine to vine. As the bacteria multiply inside the plant, they plug the xylem vessels, inhibiting water and nutrient transport throughout the plant. Infected vines die for reasons related to water uptake. The symptoms of PD therefore resemble those of water stress and include the drying, marginal burning, or scorching of leaves due to initial clogging of fine vessel elements, and eventual dieback of the vine due to total occlusion of the vessels in the trunk. Other symptoms include the shriveling and dying of fruit clusters.

Three transgenic grapevines expressing the Shiva-1 construct have been evaluated for resistance to *X. fastidiosa*. These included a non-transformed control; a transformed grapevine containing one Shiva-1 insert (designated clone B); and a transgenic grapevine containing four Shiva-1 inserts (designated clone A). Each of these plants were vegetatively propagated and then inoculated with *X. fastidiosa* according to the methods described by Hopkins (*Phytopathology* 75:713–717, 1985). While replicate plants of all three clones eventually succumbed to PD, clone A was observed to exhibit milder PD symptomology, which did not include the typical signs of marginal leaf burn when compared to the non-transformed control plant. Instead the leaves of clone A slowly became chlorotic, without signs of marginal burn. A second series of inoculations were performed with the same results. In addition, the growth of bacteria in the transgenic clones was evaluated and compared to the non-transformed control plant. Although bacteria were eventually found in the leaves of both transgenic and non-transformed plants, the spread of bacteria was slower in clone A. Our results therefore indicate that transgenic grapevine expressing the lytic peptide Shiva-1 are effective at inhibiting PD.

The methods of the invention are also useful for providing resistance to other grapevine diseases. Transgenic grapevines expressing a transgene containing a lytic peptide (e.g., Shiva-1 or cecropin B) or TomRSV-CP or both are operably linked to a constitutive promoter or to a controllable promoter such as a tissue-specific promoter, cell-type specific promoter, or to a promoter that is induced by an external signal or agent such as a pathogen- or wound-inducible control element, thus limiting the temporal or tissue expression or both. Such transgenes may also be expressed in roots, leaves, or fruits, or at a site of a grapevine that is susceptible to pathogen penetration and infection. For example, a lytic peptide gene may be engineered for constitutive low level expression in xylem-tissue expression and then transformed into a *Vitis* host plant. To achieve pathogen resistance or disease resistance or both, it is important to express the transgene at an effective level. Evaluation of the level of pathogen protection conferred to a plant by expression of such a transgene is determined according to conventional methods and assays as described herein.

In one working example, expression of a lytic peptide (e.g., Shiva-1 or cecropin B) is used to control bacterial infection, for example, to control *Agrobacterium*, the causative agent of crown gall disease. Specifically, the Shiva-1 expression vector described herein or a plant expression vector containing the cecropin B gene is used to transform somatic embryos according to the methods described above. To assess resistance to *Agrobacterium* infection and crown gall formation, transformed plants and appropriate controls are grown, and the stems are inoculated with a suspension of *Agrobacterium* according to standard methods. Transformed grape plants are subsequently incubated in a growth chamber, and the inoculated stems are analyzed for signs of resistance to crown gall formation according to standard methods. For example, the number of galls per inoculation are recorded and evaluated after inoculation. From a statistical analysis of these data, levels of resistance to *Agrobacterium* and crown gall formation are determined. Transformed grape plants that express a lytic peptide (e.g., Shiva-1 or cecropin B or both) having an increased level of resistance to *Agrobacterium* or crown gall disease or both relative to control plants are taken as being useful in the invention.

By "increased level of resistance" is meant a greater level of resistance or tolerance to a disease-causing pathogen or pest in a transgenic grapevine (or scion, rootstock, cell, or seed thereof) than the level of resistance or tolerance or both relative to a control plant (for example, a non-transgenic grapevine). In preferred embodiments, the level of resistance in a transgenic plant of the invention is at least 5–10% (and preferably 30% or 40%) greater than the resistance of a control plant. In other preferred embodiments, the level of resistance to a disease-causing pathogen is 50% greater, 60% greater, and more preferably even 75% or 90% greater than a control plant; with up to 100% above the level of resistance as compared to a control plant being most preferred. The level of resistance or tolerance is measured using conventional methods. For example, the level of resistance to a pathogen may be determined by comparing physical features and characteristics (for example, plant height and weight, or by comparing disease symptoms, for example, delayed lesion development, reduced lesion size, leaf wilting, shriveling, and curling, decay of fruit clusters, water-soaked spots, leaf scorching and marginal burning, and discoloration of cells) of transgenic grape plants.

In another working example, constitutive expression of a lytic peptide (e.g., Shiva-1 or cecropin B) is used to control the fungus *Botrytis*, the causative agent of bunch rot disease. Specifically, a plant expression vector is constructed that contains a transgene sequence that expresses the lytic peptide(s). This expression vector is then used to transform somatic embryos according to the methods described above. To assess resistance to fungal infection, transformed plants and appropriate controls are grown to approximately 30 cm vinelength, and young leaves and shoots are inoculated with a mycelial suspension of *Botrytis*. For example, plugs of *Botrytis* mycelia are inoculated on each side of the leaf midvein of developing leaves. Plants are subsequently incubated in a growth chamber at 30° C. with constant fluorescent light and high humidity. Leaves of transformed and control grapevines are then evaluated for resistance to *Botrytis* infection and disease according to conventional experimental methods. For this evaluation, for example, the number of lesions per leaf and percentage of leaf area infected are recorded every twenty-four hours for seven days after inoculation. From these data, levels of resistance to *Botrytis* are determined. In addition, if desired, fruit clusters can be sprayed with a suspension of *Botrytis* and infection monitored at 15–20° C. at 90% relative humidity after fifteen to twenty-four hours. Transformed grapevines that express a lytic peptide gene having an increased level of resistance to *Botrytis* and infection and disease relative to control plants are taken as being useful in the invention.

Alternatively, to assess resistance at the whole plant level, transformed and control grapevines are transplanted to potting soil containing an inoculum of *Botrytis*. Plants are then evaluated for symptoms of fungal infection (for example, wilting or decayed leaves) over a period of time lasting from several days to weeks. Again, transformed grapevines expressing the lytic peptide gene(s) having an increased level of resistance to the fungal pathogen, *Botrytis*, relative to control plants are taken as being useful in the invention.

OTHER EMBODIMENTS

The invention further includes analogs of any naturally-occurring lytic peptide. Analogs can differ from the naturally-occurring lytic peptide by amino acid sequence differences, by post-translational modifications, or by both. In preferred embodiments, lytic peptide analogs used in the invention will generally exhibit about 30%, more preferably 50%, and most preferably 60% or even having 70%, 80%, or 90% identity with all or part of a naturally-occurring lytic peptide amino acid sequence. The length of sequence comparison is at least 10 to 15 amino acid residues, preferably at least 25 amino acid residues, and more preferably more than 35 amino acid residues. Modifications include chemical derivatization of polypeptides, e.g., acetylation, carboxylation, phosphorylation, or glycosylation; such modifications may occur during polypeptide synthesis or processing or following treatment with isolated modifying enzymes. Lytic peptide analogs can also differ from the naturally-occurring by alterations in primary sequence. These include genetic variants, both natural and induced (for example, resulting from random mutagenesis by irradiation or exposure to ethyl methylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., $\beta$ or $\gamma$ amino acids.

In addition to full-length lytic peptides, the invention also includes peptide fragments. As used herein, the term "fragment," means at least 10 contiguous amino acids, preferably at least 15 contiguous amino acids, more preferably at least 20 contiguous amino acids, and most preferably at least 30 to 40 or more contiguous amino acids. Fragments of lytic peptides can be generated by methods known to those skilled in the art or may result from normal protein processing (e.g., removal of amino acids from the nascent polypeptide that are not required for biological activity or removal of amino acids by alternative mRNA splicing or alternative protein processing events).

All publications mentioned in this specification are herein incorporated by reference to the same extent as if each independent publication or patent application was specifically and individually indicated to be incorporated by reference.

The invention claimed is:

1. A method for increasing resistance to fungal disease in a grape plant cell, said method comprising transforming said grape plant cell with a nucleic acid molecule which encodes a lytic peptide, wherein said lytic peptide comprises the cecropin B peptide Shiva-1, wherein expression of said peptide in said grape plant cell increases resistance of said grape plant cell to fungal disease.

2. The method of claim 1, further comprising propagating a grape plant from said plant cell.

3. The method of claim 1, wherein said plant cell is a scion cell.

4. The method of claim 1, wherein said plant cell is a rootstock cell.

5. The method of claim 1, wherein said plant cell is of the Thompson seedless grape.

6. The method of claim 1, wherein said fungal disease is bunch rot disease.

7. A grape plant comprising a nucleic acid molecule which encodes a lytic peptide, wherein said lytic peptide comprises the cecropin B peptide Shiva-1, wherein expression of said peptide in said grape plant increases resistance of said grape plant to fungal disease.

8. The plant of claim 7, wherein said nucleic acid molecule comprises an expression vector.

9. The plant of claim 7, wherein said plant is a scion cultivar.

10. The plant of claim 7, wherein said plant is a rootstock cultivar.

11. The plant of claim 7, wherein said plant is of the Thompson seedless grape.

12. The plant of claim 7, wherein said fungal disease is bunch rot disease.

13. A grape plant tissue wherein a cell of said tissue comprises a nucleic acid molecule which encodes a lytic peptide, wherein said lytic peptide comprises the cecropin B peptide Shiva-1, wherein expression of said peptide in said cell increases resistance of said grape plant tissue to fungal disease.

14. The grape plant tissue of claim 13, wherein said plant tissue is a scion, a rootstock, a seed, or a somatic embryo.

15. The grape plant tissue of claim 13, wherein said nucleic acid molecule comprises an expression vector.

16. The grape plant tissue of claim 13, wherein said plant is of the Thompson seedless grape.

17. The grape plant tissue of claim 13, wherein said fungal disease is bunch rot disease.

18. The method according to claim 6, wherein said bunch rot disease is caused by the fungus *Botrytis*.

19. The method according to claim 12, wherein said bunch rot disease is caused by the fungus *Botrytis*.

20. The method according to claim 17, wherein said bunch rot disease is caused by the fungus *Botrytis*.

* * * * *

UNITED STATES PATENT AND TRADEMARK OFFICE
CERTIFICATE OF CORRECTION

PATENT NO. : 7,151,203 B2
APPLICATION NO. : 10/441669
DATED : December 19, 2006
INVENTOR(S) : Ralph Scorza and Dennis J. Gray Page 1 of 1

It is certified that error appears in the above-identified patent and that said Letters Patent is hereby corrected as shown below:

Column 6,
Line 1, "5,000 xg," should read --5,000 x g,--

Column 12,
Line 13 "Thompson seedless grape." should read --genus *Vitus*.--

Column 13,
Line 8 "Thompson seedless grape." should read --genus *Vitus*.--

Column 14,
Line 6 "Thompson seedless grape." should read --genus *Vitus*.--

Signed and Sealed this

Fourth Day of September, 2007

JON W. DUDAS
*Director of the United States Patent and Trademark Office*